United States Patent
Ono et al.

(10) Patent No.: US 8,118,430 B2
(45) Date of Patent: Feb. 21, 2012

(54) OPTHALMOLOGIC IMAGING APPARATUS AND OPTHALMOLOGIC IMAGING METHOD

(75) Inventors: Shigeaki Ono, Tokyo (JP); Hiroshi Itoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/047,617

(22) Filed: Mar. 14, 2011

(65) Prior Publication Data

US 2011/0164219 A1    Jul. 7, 2011

Related U.S. Application Data

(63) Continuation of application No. 12/831,030, filed on Jul. 6, 2010, now Pat. No. 7,926,946.

(30) Foreign Application Priority Data

Jul. 9, 2009   (JP) .................................. 2009-162824
Jun. 24, 2010  (JP) .................................. 2010-144217

(51) Int. Cl.
*A61B 3/14*   (2006.01)
*A61B 3/10*   (2006.01)
*A61B 3/00*   (2006.01)

(52) U.S. Cl. ......... 351/206; 351/205; 351/211; 351/246
(58) Field of Classification Search .......... 351/205–246; 382/281, 294, 115; 600/300, 473–477
See application file for complete search history.

(56) References Cited

U.S. PATENT DOCUMENTS

| 4,690,525 | A | 9/1987 | Kobayashi |
| 5,530,494 | A | 6/1996 | Ogawa |
| 5,905,563 | A * | 5/1999 | Yamamoto ............ 351/210 |
| 6,244,710 | B1 | 6/2001 | Ogawa |
| 7,167,771 | B2 * | 1/2007 | Ito .................... 700/182 |
| 7,429,107 | B2 * | 9/2008 | Mizuochi ............. 351/206 |

FOREIGN PATENT DOCUMENTS

| JP | S60-137347 A | 7/1985 |
| JP | S61-203937 A | 9/1986 |
| JP | H02-237536 A | 9/1990 |
| JP | H03-114434 A | 5/1991 |
| JP | H04-150831 A | 5/1992 |
| JP | 05-064075 A | 3/1993 |
| JP | H05-192299 A | 8/1993 |
| JP | H08-033612 A | 2/1996 |
| JP | H11-238129 A | 8/1999 |
| JP | 2000-107133 A | 4/2000 |

(Continued)

*Primary Examiner* — Mohammed Hasan
(74) *Attorney, Agent, or Firm* — Canon U.S.A., Inc., IP Division

(57) ABSTRACT

An ophthalmologic imaging apparatus that captures a fundus image of a subject's eye includes a first extraction unit configured to extract, from a first fundus image photographed with a first light quantity, an image of a first area having intensity not less than predetermined intensity and an image of a second area other than the first area, a second extraction unit configured to extract an image of an area corresponding to the first area from a second fundus image photographed with a second light quantity based on the light quantity of the first area, a third extraction unit configured to extract an image of an area corresponding to the second area from a third fundus image photographed with a third light quantity based on the light quantity of the second area, and an image combining unit configured to combine the images extracted by the second and the third extraction units.

19 Claims, 11 Drawing Sheets

FOREIGN PATENT DOCUMENTS

| | | |
|---|---|---|
| JP | 2000-197608 A | 7/2000 |
| JP | 2001-258852 A | 9/2001 |
| JP | 2003-010134 A | 1/2003 |
| JP | 2003-010134 A | 1/2003 |
| JP | 2005-261447 A | 9/2005 |
| JP | 2005-261449 A | 9/2005 |
| JP | 2005-270152 A | 10/2005 |
| JP | 2005-279154 A | 10/2005 |
| JP | 2008-132239 A | 6/2008 |

* cited by examiner

OPTHALMOLOGIC IMAGING APPARATUS AND OPTHALMOLOGIC IMAGING METHOD

CROSS REFERENCE TO RELATED APPLICATIONS

This application is a Continuation of U.S. patent application Ser. No. 12/831,030 filed Jul. 6, 2010 now U.S. Pat. No. 7,926,946 B2, which claims priority to Japanese Patent Application No. 2010-144217 filed Jun. 24, 2010 and Japanese Patent Application No. 2009-162824, filed Jul. 9, 2009 each of which are hereby incorporated by reference in their entireties.

BACKGROUND OF THE INVENTION

1. Field of the Invention

The present invention relates to an ophthalmologic imaging apparatus and an ophthalmologic imaging method that captures a fundus of a subject's eye.

2. Description of the Related Art

Japanese Patent Application Laid-Open No. 2000-107133 discusses a fundus camera that can photograph a fundus by adequately shading a bright portion and a dark portion of the fundus within a photographing field of view, even if an exposure condition is unclear. This is a technique of causing a photographing light source to emit a strong light and a weak light alternately, when a fundus is subjected to fluorescence photography, since fluorescent intensity is significantly different between a thick blood vessel and a thin blood vessel.

Japanese Patent Application Laid-Open No. 2003-10134 discusses a fundus camera that can illuminate only an optic papilla with a visible light to adjust focusing in the optic papilla without contracting a pupil of a subject's eye.

However, Japanese Patent Application Laid-Open No. 2000-107133 does not discuss that a quantity of emitted light is adjusted according to a portion to be photographed, when the photographing light source is allowed to emit a strong light and a weak light. Further, the image obtained in Japanese Patent Application Laid-Open No. 2003-10134 is not a fundus image in which both the optic papilla and the portion other than the optic papilla are brought into focus, so that the image has an insufficient image quality for diagnosis.

It is considered here that an optic papilla and a macula are simultaneously photographed as a single fundus image, when the fundus is photographed. When the optic papilla is properly exposed, the macula is totally underexposed. On the contrary, when the macula is properly exposed, the optic papilla is totally overexposed. This is because the optic papilla is the brightest, and the macula is the darkest in the photographing field of view of the fundus, and a dynamic range of an image sensor is insufficient to simultaneously photograph both portions.

It is then considered the case in which the optic papilla is photographed with a visible light, while the macula is photographed with an infrared light, and then, both images are combined to form a fundus image. In this case, the combined image has an insufficient image quality for diagnosis, since these two images are not photographed with the same light quantity.

SUMMARY OF THE INVENTION

According to an aspect of the present invention, an opthalmologic imaging apparatus that captures an image of a fundus of a subject's eye includes a first extraction unit configured to extract, from a first fundus image photographed with a first light quantity, an image of a first area having intensity not less than predetermined intensity and an image of a second area other than the first area, a second extraction unit configured to extract an image of an area corresponding to the first area from a second fundus image photographed with a second light quantity based on the light quantity of the first area, a third extraction unit configured to extract an image of an area corresponding to the second area from a third fundus image photographed with a third light quantity based on the light quantity of the second area, and an image combining unit configured to combine the images extracted by the second and the third extraction units.

According to another aspect of the present invention, a method for an ophthalmologic imaging to capture an image of a fundus of a subject's eye includes a first extracting step for extracting, from a first fundus image photographed with a first light quantity, an image of a first area having intensity not less than predetermined intensity and an image of a second area other than the first area, a second extracting step for extracting an image of an area corresponding to the first area from a second fundus image photographed with a second light quantity based on the light quantity of the first area, a third extracting step for extracting an image of an area corresponding to the second area from a third fundus image photographed with a third light quantity based on the light quantity of the second area, and a combining step for combining the images which are extracted in the second and third extracting steps.

According to the ophthalmologic imaging apparatus and the ophthalmologic imaging method according to the present invention, areas (mainly, an area including an optic papilla and another area including a lutea) having different brightness in a fundus of a subject's eye can be photographed with a proper light quantity. When these images are combined, a fundus image having an image quality sufficient for diagnosis can be acquired.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Exemplary embodiments of an ophthalmologic imaging apparatus and an ophthalmologic imaging method according to the present invention will be described in detail below with reference to the drawings.

Figure 1:
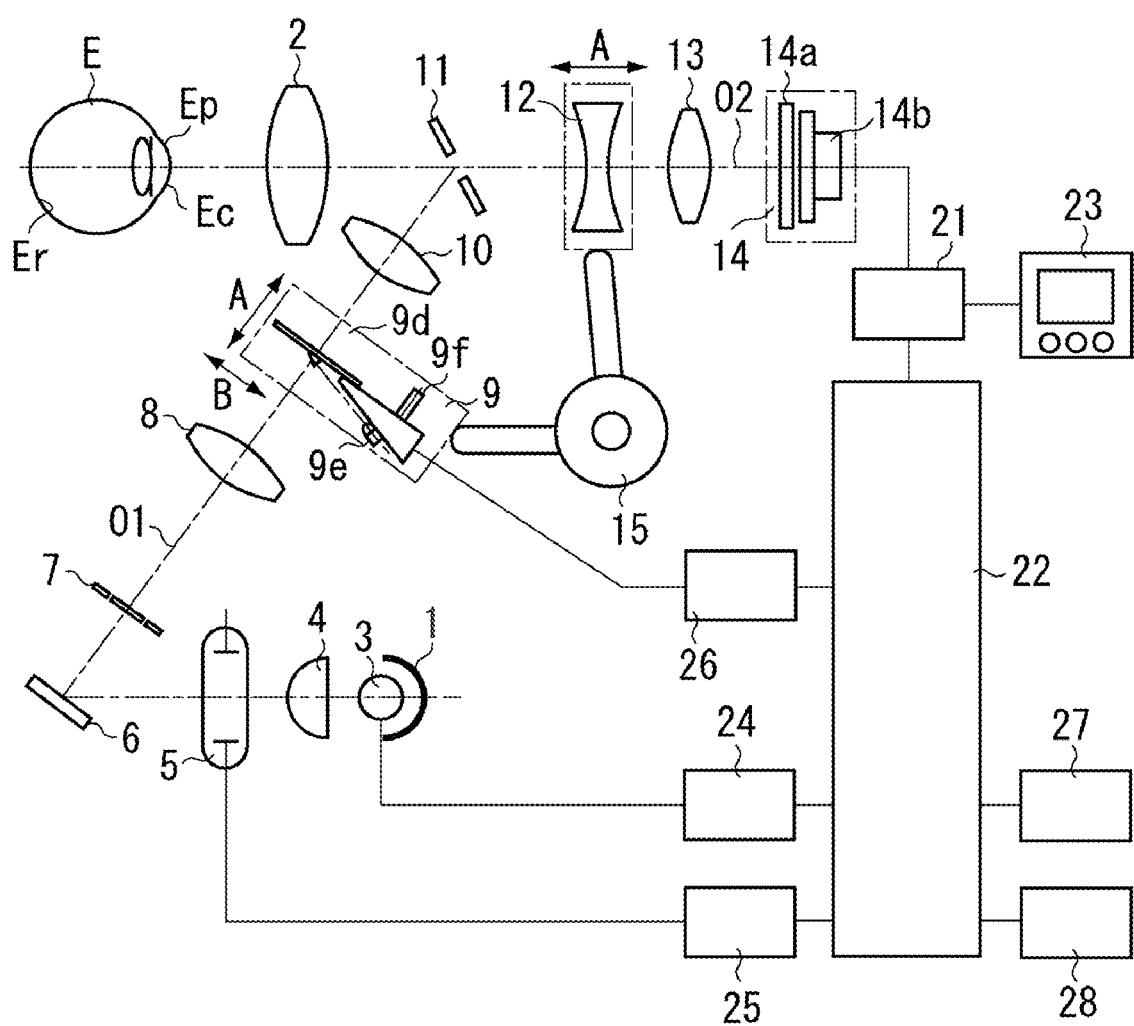
FIG. 1 illustrates a configuration of a fundus camera according to a first exemplary embodiment of the present invention.

FIG. 1 illustrates a configuration of a fundus camera according to a first exemplary embodiment. An observation light source 3 including a halogen lamp, a condenser lens 4, a photographing light source 5 including a xenon tube, and a mirror 6 are arranged on an optical path O1 of an illumination optical system from a reflector 1 to an objective lens 2 located opposite to a subject's eye E. A diaphragm 7 having an ring shaped opening, a relay lens 8, a focus index projection unit 9, a relay lens 10, and a perforated mirror 11 are sequentially arranged in a reflecting direction of the mirror 6.

A focusing lens 12, a photographic lens 13, a three-color wavelength separation unit 14a, and an imaging unit 14 including an image sensor 14b are sequentially arranged on an optical path O2 of an observation/photographing optical system at the rear of the perforated mirror 11. The focus index projection unit 9 and the focusing lens 12 are moved in conjunction with each other by a focus link mechanism 15.

An output of the imaging unit 14 is connected to a control unit 22 that controls a photographing operation via an image signal processing unit 21, and an output of the image signal processing unit 21 is connected to a display unit 23 that displays an image. An output of the control unit 22 is connected to the observation light source 3, the photographing light source 5, and the focus index projection unit 9 respectively via an observation light source driving circuit 24, a photographing light source driving circuit 25, and a focus index control circuit 26. An input unit 27 and a recording unit 28 are also connected to the control unit 22.

Figure 2:
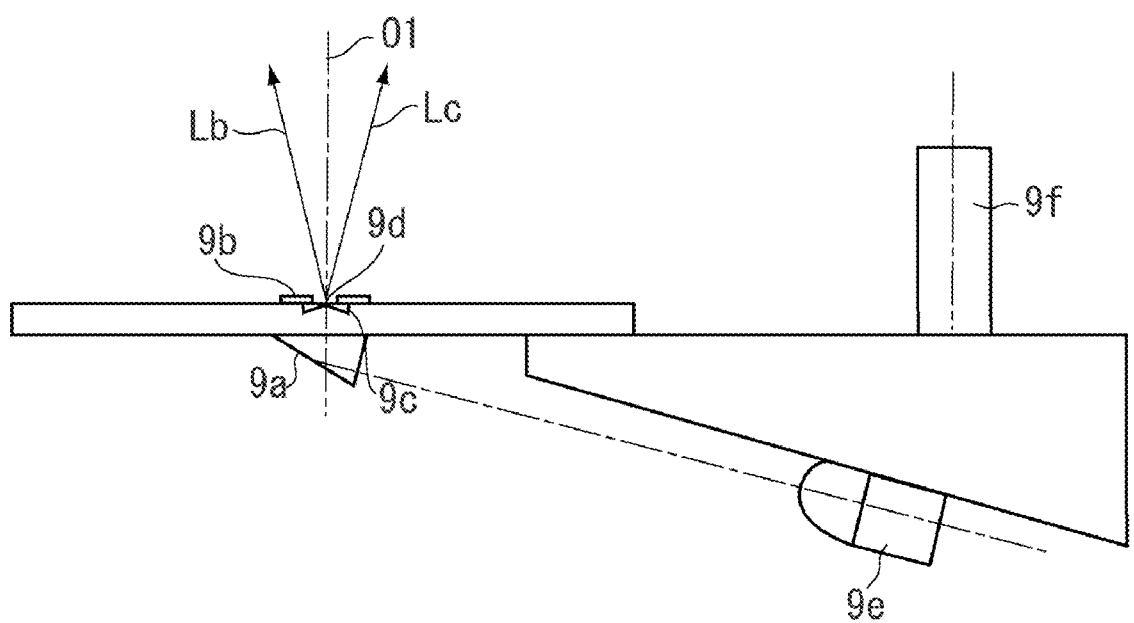
FIG. 2 is an enlarged side view of a focus index projection unit.
Figure 3:
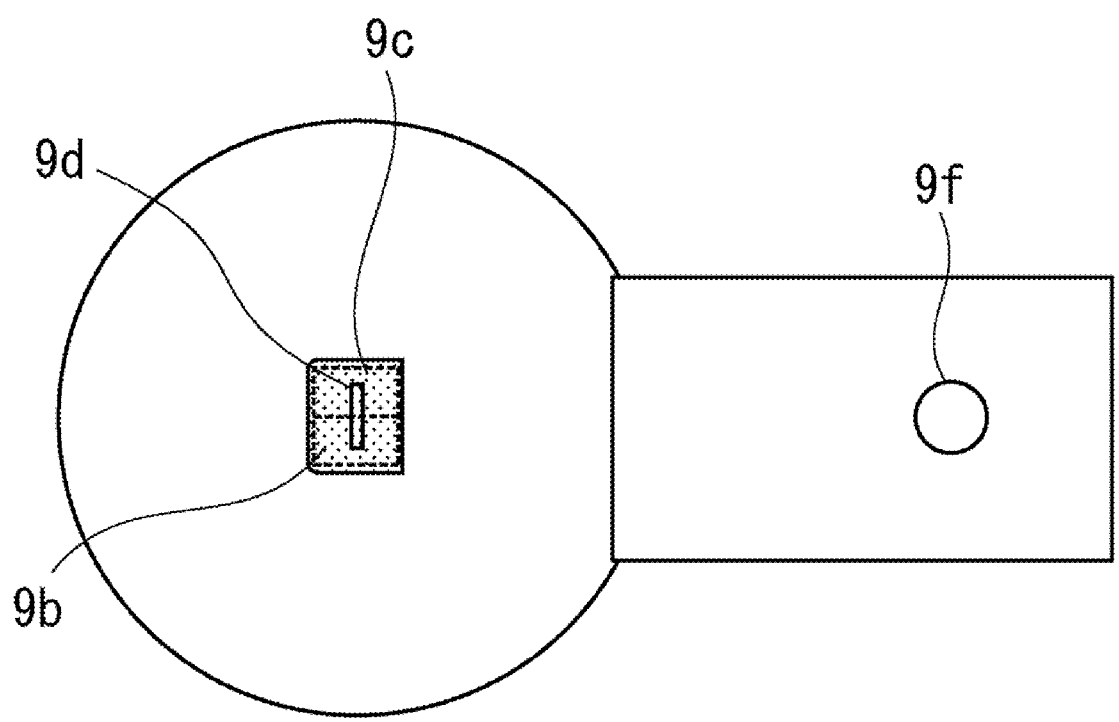
FIG. 3 is an enlarged front view of the focus index projection unit.

FIG. 2 is an enlarged side view of the focus index projection unit 9. FIG. 3 is an enlarged front view of the focus index projection unit 9. The focus index projection unit 9 includes a focus split prism having prism portions 9a, 9b, and 9c, a focus index 9d having a rectangular opening, and a focus index light source 9e. The prism portions 9b and 9c have prism surfaces whose angles are symmetric with each other. The focus index light source 9e includes a light-emitting diode (LED) having a center wavelength in a visible light.

The focus index projection unit 9 moves in a direction A indicated in FIG. 1 in conjunction with the focusing lens 12 by the focus link mechanism 15, so that the focus index 9d of the focus index projection unit 9 and the image sensor 14b of the imaging unit 14 have an optical conjugate relation. When a still image is photographed, the focus index projection unit 9 rotates about an axis 9f to move in the direction B in FIG. 1, thereby retracting from the optical path O1 of the illumination optical system.

During the observation of a fundus, a light flux emitted from the observation light source 3 passes through the condenser lens 4, the mirror 6, the diaphragm 7, the relay lens 8, the focus index projection unit 9, and the relay lens 10 and reflected around the perforated mirror 11. Further, the light flux illuminates a fundus Er through a cornea Ec and a pupil Ep of the subject's eye E via the objective lens 2. The control unit 22 controls the focus index control circuit 26 to turn on the focus index light source 9e of the focus index projection unit 9.

As illustrated in FIG. 2, the light flux from the focus index light source 9e is polarized in the direction of the optical path O1 by the prism portion 9a of the focus split prism, reaches the prism portions 9b and 9c, and is branched in two directions. The light flux further passes through the rectangular opening of the focus index 9d to become two focus index light fluxes Lb and Lc which are symmetric with each other to the optical path O1 and reaches the fundus Er of the subject's eye E via the relay lens 10, the perforated mirror 11, and the objective lens 2.

Figure 4A:
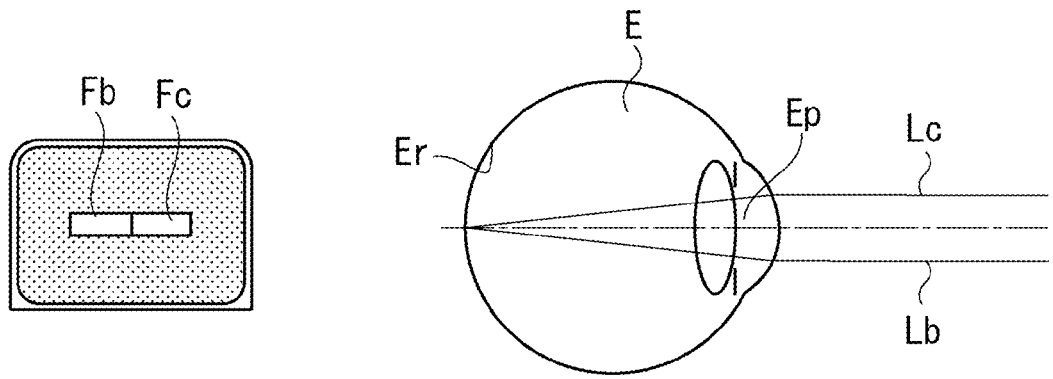
FIGS. 4A to 4C illustrate a state in which a focus index light flux reaches a fundus of a subject's eye, and a focus index image on the fundus by the focus index light flux.
Figure 4B:
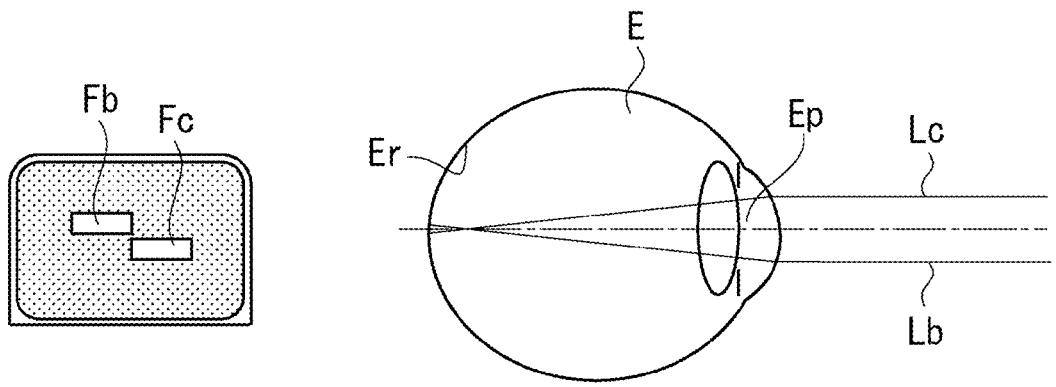
Figure 4C:
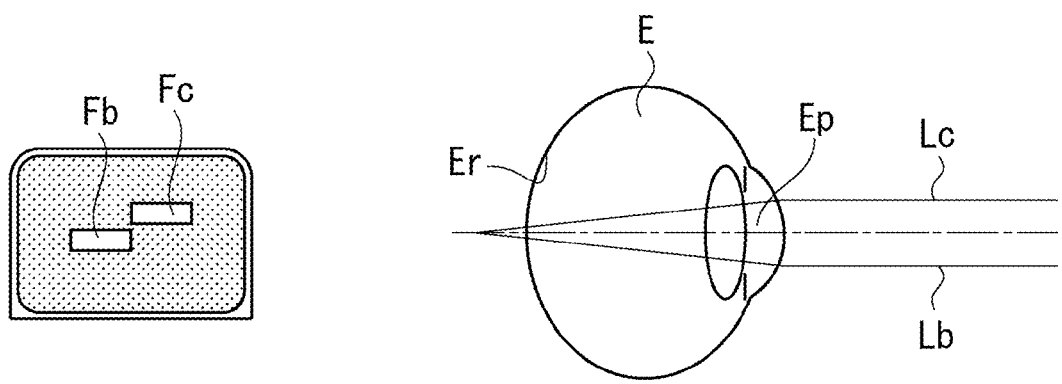

Each of FIGS. 4A to 4C illustrates a state in which the focus index light fluxes Lb and Lc reach the fundus Er, and focus index images Fb and Fc on the fundus Er formed by the focus index light fluxes Lb and Lc. FIG. 4A illustrates the case in which the fundus Er and the focus index 9d are in an optical conjugate relation. Since the fundus Er and the focus index 9d are in the optical conjugate relation, the two separated focus index light fluxes Lb and LC form the images Fb and Fc of the rectangular opening of the focus index 9d on the fundus Er, and they are arranged side by side.

FIG. 4B illustrates the case in which the subject's eye E is myopic more than the case in FIG. 4A. Since the fundus Er and the focus index 9d are not in the optical conjugate relation, the two separated focus index light fluxes Lb and Lc form the images Fb and Fc of the rectangular opening of the focus index 9d on the fundus Er, and they are shifted from each other in a vertical direction, wherein the image Fb is shifted upward and the image Fc is shifted downward.

FIG. 4C illustrates the case in which the subject's eye E is hyperopic more than the case in FIG. 4A. Since the fundus Er and the focus index 9d are not in the optical conjugate relation, the two separated focus index light fluxes Lb and Lc form the images Fb and Fc of the rectangular opening of the focus index 9d on the fundus Er, and they are shifted from each other in the vertical direction, wherein the image Fb is shifted downward and the image Fc is shifted upward.

An illuminated fundus image Er' and the index images Fb and Fc passes through the pupil Ep, a cornea Ec, the objective lens 2, and holes of the perforated mirror 11, the focusing lens 12, and the photographic lens 13, reaches the image sensor 14b via the three-color wavelength separation unit 14a in the imaging unit 14, and form images thereon.

Figure 5:
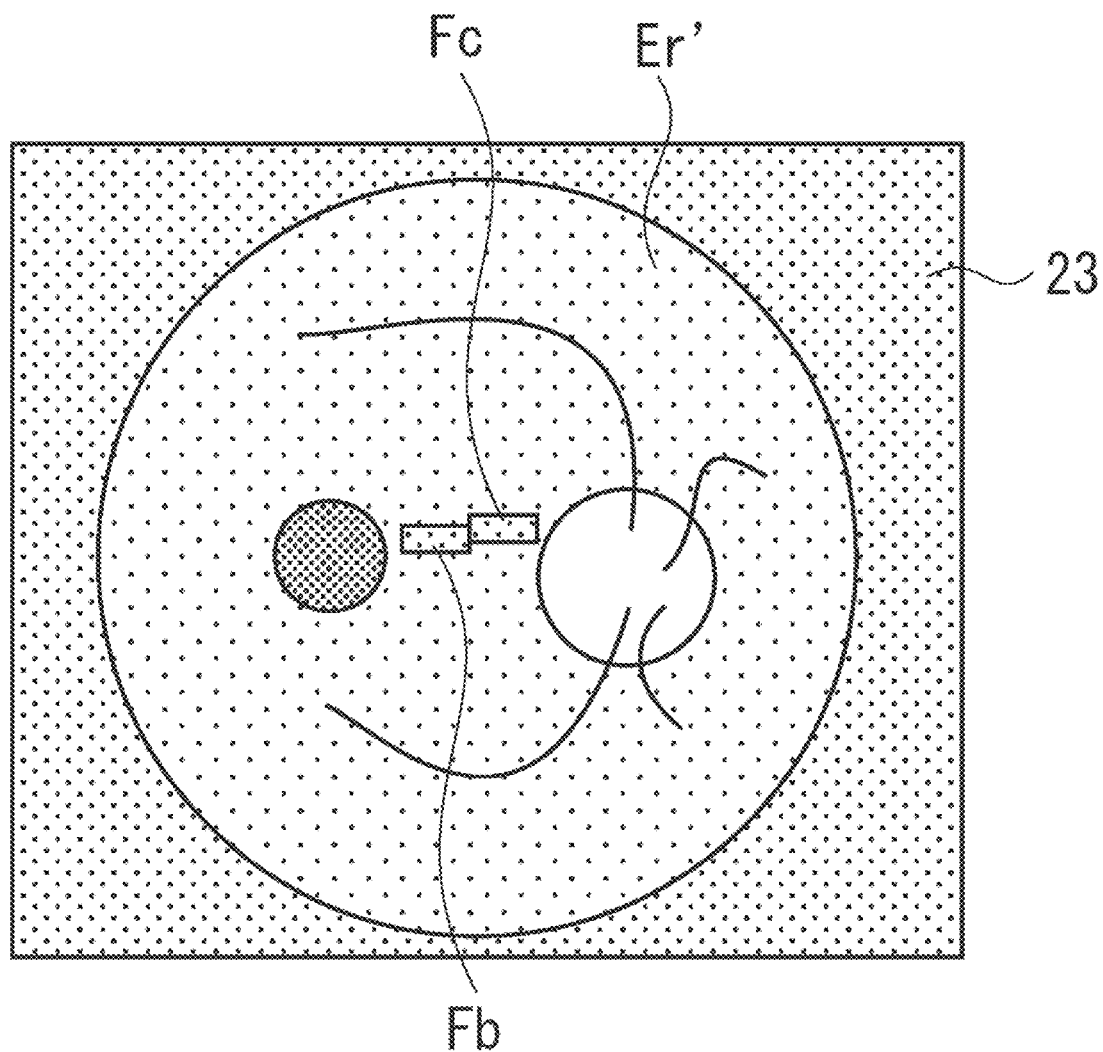
FIG. 5 illustrates a display screen of a display unit according to the first exemplary embodiment.

The image sensor 14b performs a photoelectric conversion to the fundus image Er' as a reflected image of the fundus Er, and the focus index images Fb and Fc. The image signal processing unit 21 reads data from the image sensor 14b, and performs amplification and A/D conversion on the data, so that digital image data is generated. The generated digital image data is input to the control unit 22, and simultaneously, displayed on the display unit 23 as a moving image as illustrated in FIG. 5.

An operator observes the index images Fb and Fc of the rectangular opening of the focus index 9d displayed on the display unit 23, and operates a focus knob to arrange the focus images Fb and Fc side by side. More specifically, when the fundus Er and the focus index 9d are in the optical conjugate relation, the focus index 9d of the focus index projection unit 9 and the image sensor 14b are in an optical conjugate relation by the focus link mechanism 15 (a unit which moves a first moving unit configured to move the focus index projection unit and a second moving unit configured to move the focusing unit in conjunction with each other). Therefore, the fundus Er and the image sensor 14*b* are brought into an optical conjugate relation by moving from a first conjugate position to a second conjugate position, so that the fundus Er is brought into focus.

Figure 6:
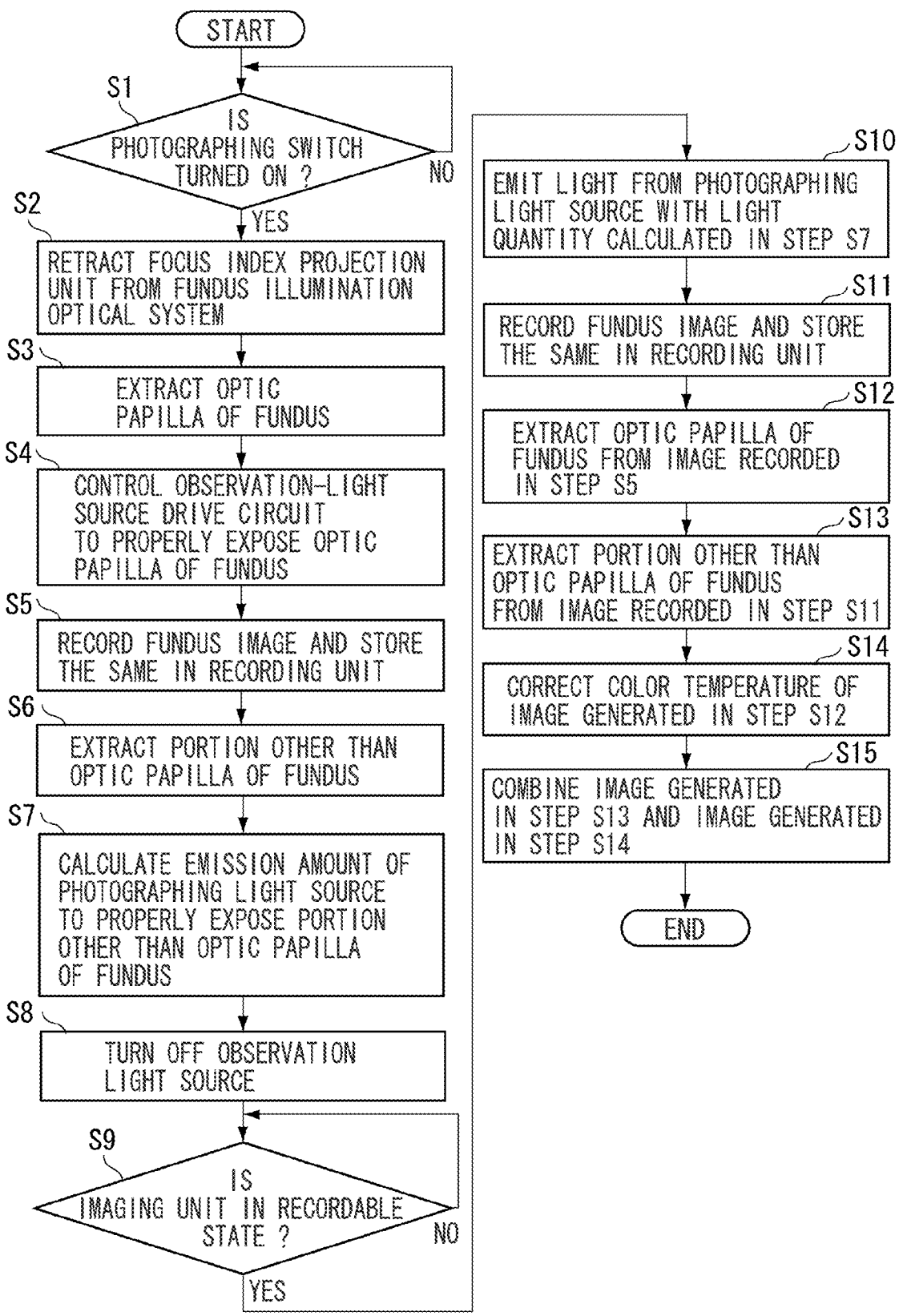
FIG. 6 is a flow chart illustrating an operation of a calculation unit according to the first exemplary embodiment.

FIG. 6 is a flow chart illustrating an operation when the fundus is photographed. The operator adjust alignment and focus, while observing the image illustrated in FIG. 5 which is displayed on the display unit 23. When the alignment is matched and the image is brought into focus, the operator presses a photographing switch of the input unit 27. (With this operation, a first fundus image can be photographed with a first light quantity.) In step S1, the control unit 22 detects the operation that the photographing switch is pressed. In step S2, the control unit 22 controls the focus index control circuit 26 to drive the focus index projection unit 9 in the direction B to retract the same from the optical path O1. In step S3, an optic papilla N (a first area) of the fundus Er is extracted (which is executed by a first extraction unit).

Figures 7A, 7B, 7C, 7D, 7E, 7F, 7G:
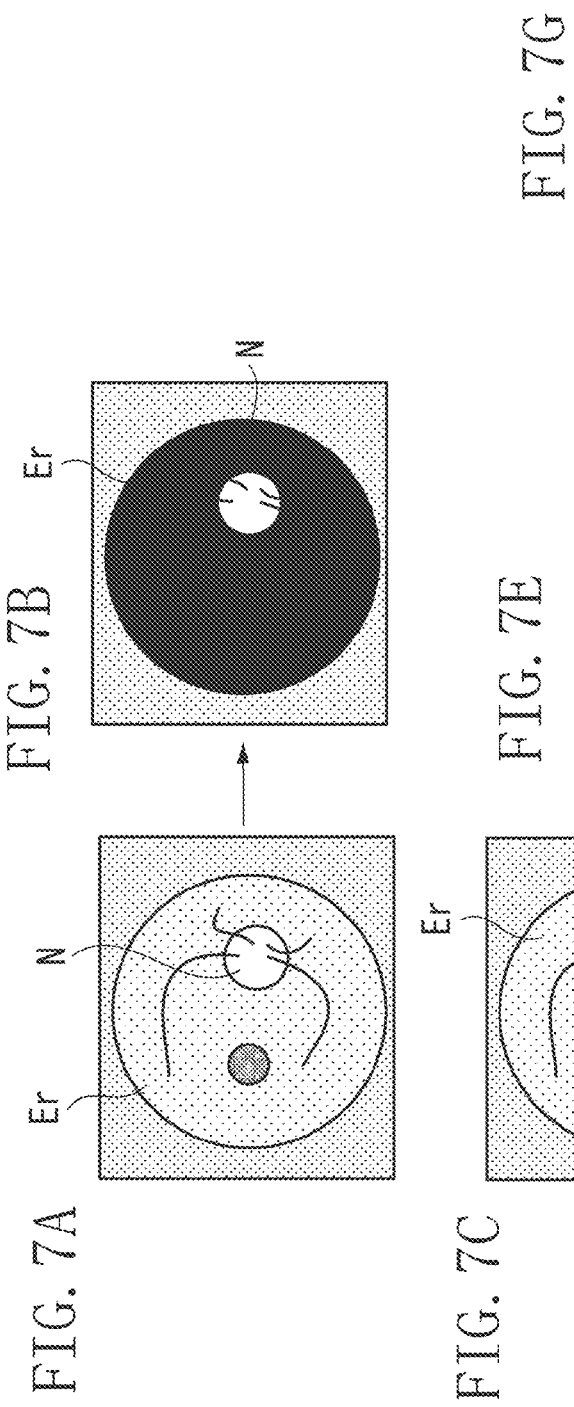
FIGS. 7A to 7G illustrate a method for detecting an optic papilla N of a fundus, and a method for combining images according to the first exemplary embodiment.

In general, the optic papilla N is the brightest part in the fundus image. Therefore, the maximum value is selected from the digital image data of the fundus image of the fundus Er as illustrated in FIG. 7A which is obtained by the imaging unit 14 and input into the control unit 22 via the image signal processing unit 21. For example, intensity (predetermined intensity) of 70% of the maximum value Dmax is defined as a reference value (which is executed by a setting unit). Then, binarization processing is performed with this reference value. FIG. 7B illustrates a result of the binarization processing. Among fundus image data pieces Dij, data having 0.7 or more of Dmax (having the intensity more than the predetermined intensity) is defined to be 255, which is the maximum value when the image data is 8 bits (0 to 255), and the data having less than 0.7 of Dmax is defined as 0 that corresponds to a black signal. In this way, the optic papilla N is extracted.

In step S4, the light quantity of the observation light source 3 (the light source that emits light with first and second light quantities) is changed by the observation light quantity control by the observation light source driving circuit 24 in order that the optic papilla N in the image in FIG. 7B extracted in step S3 has a proper light quantity (second light quantity based on the light quantity in the first area). In the present exemplary embodiment, the proper quantity is defined such that an average value Dav of the image data pieces Dij of the optic papilla N is 120. In step S5, the image data as illustrated in FIG. 7C in which the optic papilla N is properly exposed (a second fundus image photographed with the second light quantity) is recorded and stored in the recording unit 28.

In step S6, the portions (the second area other than the first area) of the fundus Er excluding the optic papilla N extracted in step S3 is extracted (which is executed by the first extraction unit). In step S7, an emission amount of the photographing light source 5 (the light source that emits light with a third light quantity) is calculated to make the portion other than the optic papilla N being properly exposed (a third light quantity based on the light quantity in the second area). Further, in step S8, the observation light source driving circuit 24 is controlled to turn off the observation light source 3. In step S9, the control unit 22 determines whether the imaging unit 14 is in a recordable state. When the imaging unit 14 is in the recordable state (YES in step S9), the processing proceeds to step S10 where the control unit 22 allows the photographing light source 5 to emit light with the light quantity (calculated result) calculated in step S7 in synchronization with the imaging unit 14 under photographing light control by the photographing light source driving circuit 25.

In step S11, the image of the fundus Er in which the portion other than the optic papilla N of the fundus Er is properly exposed (a third fundus image photographed with the third light quantity) is recorded and stored in the recording unit 28. FIG. 7D illustrates image data which is obtained in this operation. In step S12, the optic papilla N is extracted (an image of an area corresponding to the first area is extracted from the second fundus image) from the image in FIG. 7C which is recorded in step S5. FIG. 7E illustrates image data which is obtained in this operation (which is executed by a second extraction unit). In step S13, the portion other than the optic papilla N is extracted (an image of an area corresponding to the second area is extracted from the third fundus image) from the image in FIG. 7D which is recorded in step S11. FIG. 7F illustrates an image which is obtained in this operation (which is executed by a third extraction unit).

The observation light source 3 including the halogen lamp generally has a color temperature of 3000 to 3400 K, while the photographing light source 5 including the xenon tube has a color temperature of 5500 to 6000 K. The color temperatures of the respective light sources which are used to record the images in steps S5 and S11 are different, thus when the images recorded in steps S5 and S11 are combined without any change, an image having an unnatural color is formed. Accordingly, in step S14, two images are corrected to allow the image in FIG. 7E formed in step S12 to have a color temperature equal to that of the image in FIG. 7F which is photographed by the photographing light source 5.

In step S15, the images whose color temperatures are corrected in step S14 are combined to form a single fundus image. FIG. 7G illustrates image data which is obtained in this operation. The fundus image thus formed is exposed with proper exposure both at the optic papilla N and the portion other than the optic papilla N which includes a macula M.

Figure 8A:
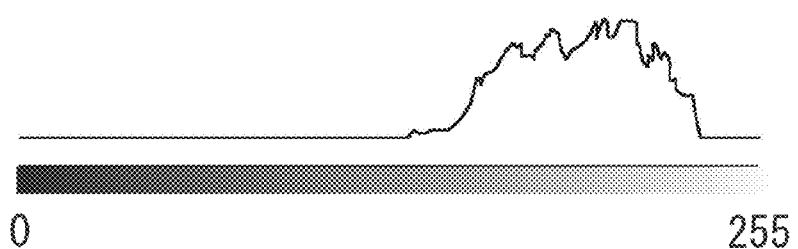
FIGS. 8A to 8C are histograms of fundus image data.
Figure 8B:
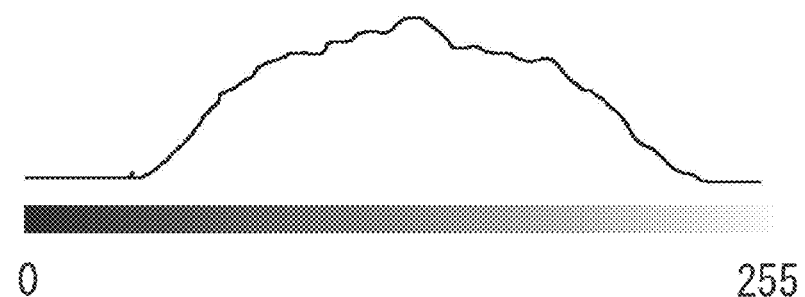
Figure 8C:
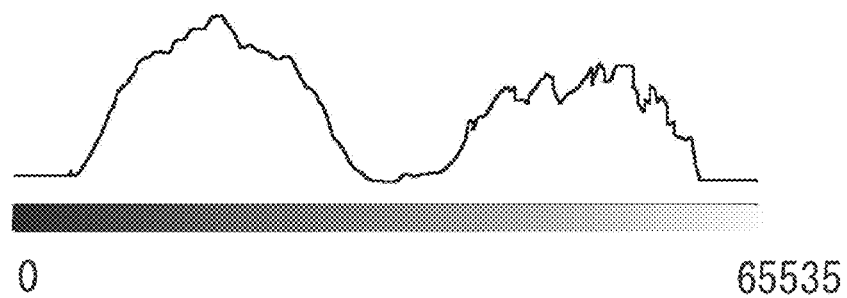

Each of FIGS. 8A to 8C illustrates a histogram of the image data for a combination of images executed in step S15 according to another exemplary embodiment. FIG. 8A is the histogram of the image data in which the optic papilla N of the fundus as illustrated in FIG. 7E is extracted. FIG. 8B is the histogram of the image data generated in step S13 in which the portion other than the optic papilla N is extracted. It is supposed that the image data has 8 bits (0 to 255), white is indicated by 255 that is the maximum value, and black is indicated by 0 that is the minimum value. When the images are combined in step S15, the image data may be extended to have 16 bits, the portion other than the optic papilla N may be allocated to the lower 8 bits, and the optic papilla N may be allocated to the higher 8 bits to perform the image combination. FIG. 8C illustrates the histogram when the images are combined as described above. The images may be combined in such a manner that a blood vessel at the portion other than the optic papilla N and a blood vessel at the optic papilla N have the same brightness.

In the present exemplary embodiment, after the image of the optic papilla N formed with using the observation light source 3 is recorded in steps S3 to S5, the image of the portion other than the optic papilla N formed with using the photographing light source 5 is recorded in steps S6 to S11. However, the order of recording may be different from the one described above. For example, after the processing in step S2 is executed, the processing in steps S6 to S11 are executed, and then, the processing in steps S3 to S5 are executed. Thereafter, the processing may proceed to step S12.

Figure 9:
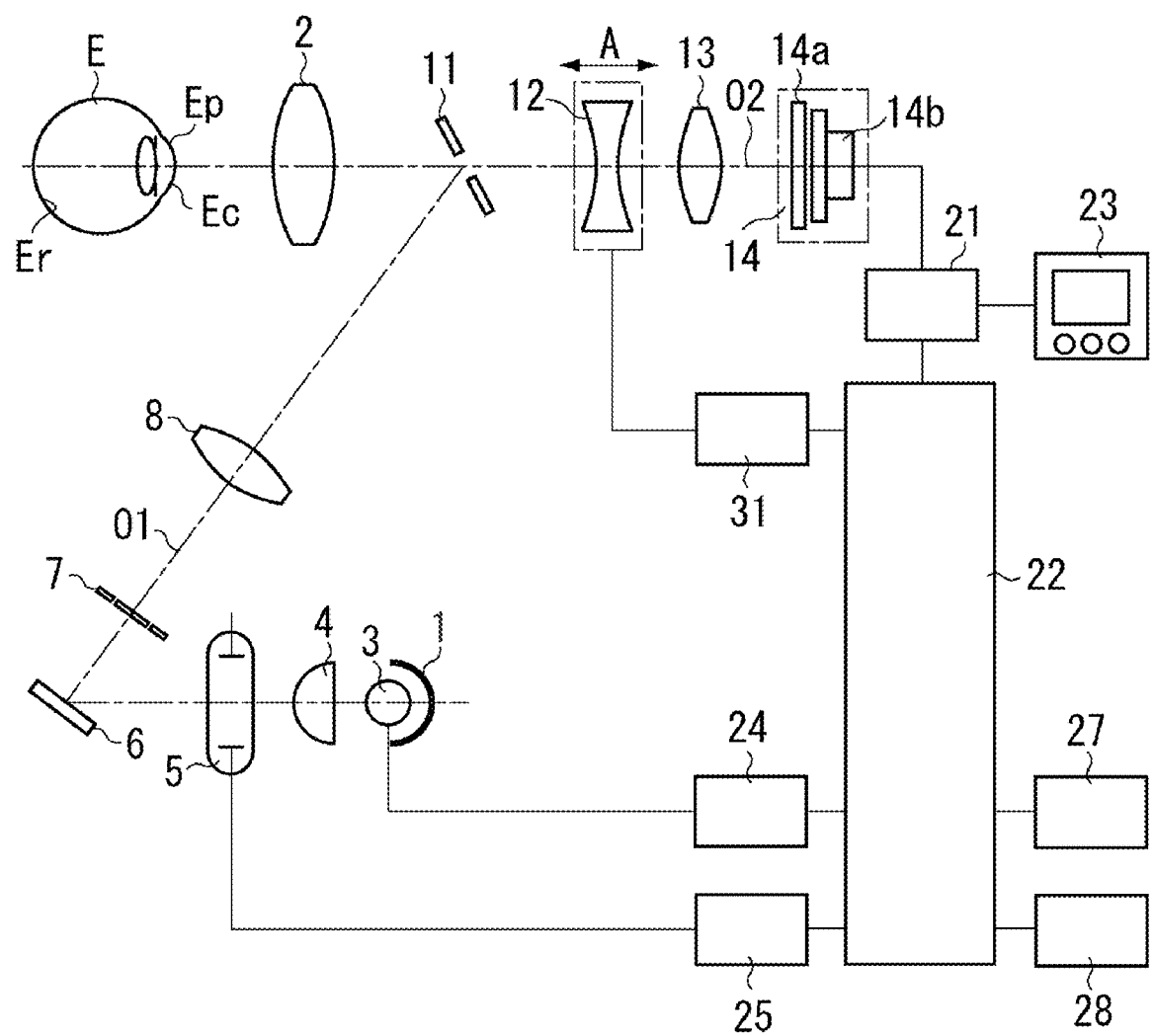
FIG. 9 illustrates a configuration of a fundus camera according to a second exemplary embodiment.

FIG. 9 illustrates a configuration of a fundus camera according to a second exemplary embodiment. In FIG. 9, the focus index projection unit 9, the relay lens 10, and the focus link mechanism 15 are removed from FIG. 1. The output of the control unit 22 is connected to the focusing lens 12 via the driving circuit 31.

Figure 10:
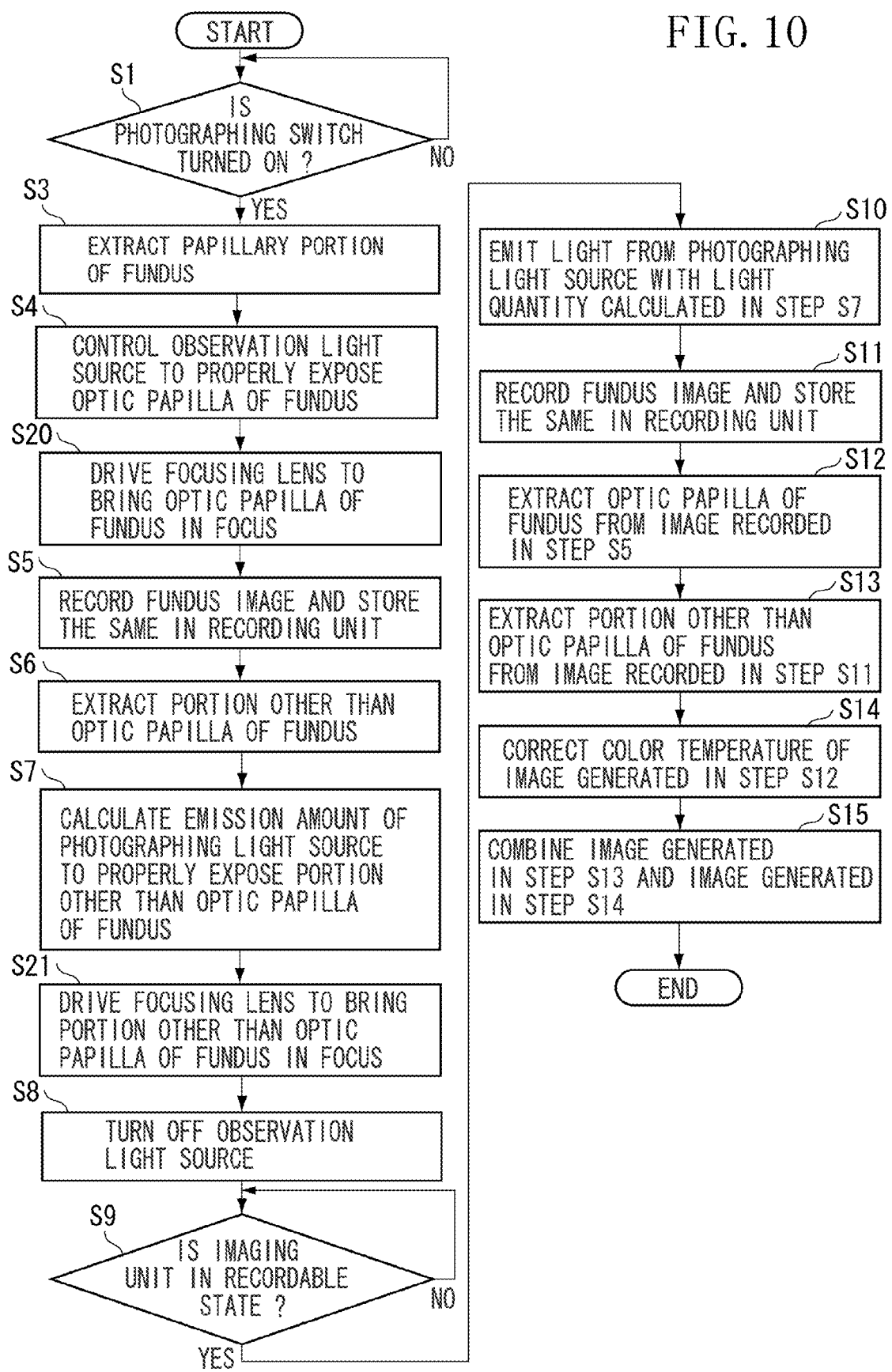
FIG. 10 is a flow chart illustrating an operation of a calculation unit according to the second exemplary embodiment.

FIG. 10 is a flow chart illustrating the operation of the control unit 22 when a fundus is photographed. Compared to the flow chart illustrated in FIG. 6, in the flow chart in FIG. 10, step S2 is deleted, step S20 for performing focusing control is added between steps S4 and S5, and step S21 for moving the focusing lens is added between steps S7 and S8.

Figure 11E:
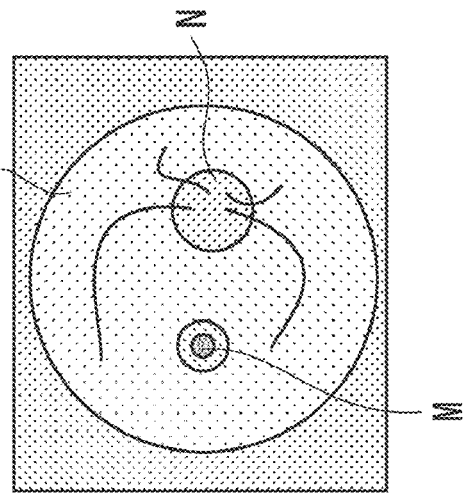
FIGS. 11A to 11E illustrate a method for combining fundus images according to the second exemplary embodiment.
Figure 11C:
Figure 11D:
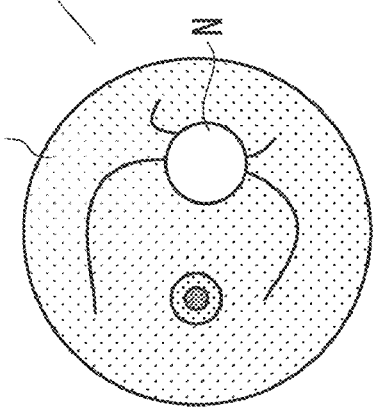
Figure 11A:
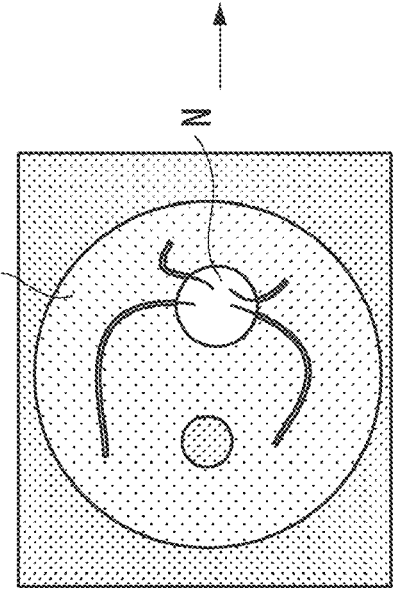

Steps S1, S3, and S4 are the same as those in the first exemplary embodiment. In step S20, the driving circuit 31 is controlled to move the focusing lens 12 in a direction of A in FIG. 9. From the fundus image which is input into the control unit 22 via the image signal processing unit 21 and formed on the image sensor 14b, the optic papilla N is extracted in step S4. A focusing position at which the image of the optic papilla N has the highest contrast is detected, and the focusing lens 12 is stopped at the focusing position. In this way, the image of the fundus Er recorded in step S5 becomes the fundus image in which the optic papilla N is properly exposed and brought into focus as illustrated in FIG. 11A.

Figure 11B:
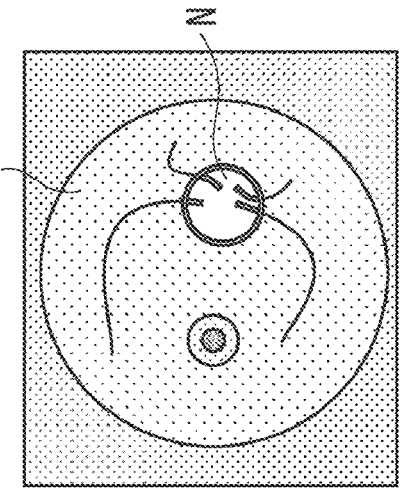

Steps S5, S6, and S7 are the same as those in the first exemplary embodiment. In step S21, the driving circuit 31 is controlled to move the focusing lens 12 by a predetermined amount. From the fundus image which is input into the control unit 22 via the image signal processing unit 21 and formed on the image sensor 14b, the portion other than the optic papilla N is extracted in step S6. The focusing lens 12 is stopped at a position at which the portion other than the optic papilla N has the highest contrast. More specifically, the focusing lens 12 is moved by the predetermined amount that is a difference between the focusing position of the optic papilla N and the focusing position of the portion other than the optic papilla N. In this way, the image of the fundus Er recorded in step S11 becomes the fundus image in which the portion other than the optic papilla N is properly exposed and brought into focus as illustrated in FIG. 11B.

Steps S8 to S15 are the same as those in the first exemplary embodiment. The image formed in step S13 as illustrated in FIG. 11C and the image formed in step S14 as illustrated in FIG. 11D are combined to form a single fundus image in step S15. This image is a fundus image in which the optic papilla N and the portion other than the optic papilla N and that includes the macula M are properly exposed and brought into focus as illustrated in FIG. 11E.

Aspects of the present invention can also be realized by a computer of a system or apparatus (or devices such as a CPU or MPU) that reads out and executes a program recorded on a memory device to perform the functions of the above-described embodiment (s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An ophthalmologic apparatus comprising:
a changing unit configured to change a light quantity of illumination light which illuminates a subject's eye based on each of areas having different brightness of a first fundus image of the subject's eye; and
an acquiring unit configured to acquire second and third fundus images of the subject's eye each illuminated by the illumination light with the changed light quantity.

2. The ophthalmologic apparatus according to claim 1, further comprising:
an extraction unit configured to extract an area corresponding to an optic papilla and an area corresponding to a macula from the first fundus image,
wherein the changing unit changes the light quantity of the illumination light for each of the area corresponding to the optic papilla and the area corresponding to the macula.

3. The ophthalmologic apparatus according to claim 2, further comprising:
wherein the acquiring unit acquires the second fundus image illuminated by observation light with a light quantity based on the area corresponding to the optic papilla, and acquires the third fundus image illuminated by photographing light with a light quantity based on the area corresponding to the macula.

4. The ophthalmologic apparatus according to claim 3, wherein the extraction unit extracts the image of the area corresponding to the optic papilla from the second fundus image of the subject's eye illuminated by the observation light, and extracts the image of the area corresponding to the macula from the third fundus image of the subject's eye illuminated by the photographing light.

5. The ophthalmologic apparatus according to claim 4, further comprising:
an image combing unit configured to combine the images extracted from the second and third fundus images.

6. An ophthalmologic apparatus comprising:
a changing unit configured to change a light quantity of an observation light based a predetermined area of a first fundus image of a subject's eye illuminated by the observation light; and
an acquiring unit configured to acquire a second fundus image of the subject's eye illuminated by the observation light with the changed light quantity.

7. The ophthalmologic apparatus according to claim 6, wherein the predetermined area is an area corresponding to an optic papilla of the fundus of the subject's eye.

8. The ophthalmologic apparatus according to claim 7, further comprising: an extraction unit configured to extract the area corresponding to the optic papilla from the first fundus image,
wherein the changing unit changes the light quantity of the observation light based on the area corresponding to the optic papilla.

9. The ophthalmologic apparatus according to claim 7, further comprising: a calculating unit configured to calculate the light quantity of the observation light based on the area corresponding to the optic papilla,
wherein the changing unit changes the light quantity of the observation light based on a calculated result of the calculating unit.

10. The ophthalmologic apparatus according to claim 6, wherein the changing unit changes a light quantity of a photographing light based on an area other than the predetermined area of the first fundus image; and
wherein the acquiring unit acquires a third fundus image of the subject's eye illuminated by the photographing light with the changed light quantity.

11. The ophthalmologic apparatus according to claim 10, further comprising:
an extraction unit configured to extract the area other than the predetermined area from the first fundus image, wherein the area other than the predetermined area is an area corresponding to a macula of the fundus of the subject's eye, and wherein the changing unit changes the light quantity of the photographing light based on the area corresponding to the macula.

12. The ophthalmologic apparatus according to claim 10, further comprising:

a first extracting unit configured to extract an image of the predetermined area and an image of the area other than the area corresponding to the predetermined area from the first fundus image;

a second extracting unit configured to extract an image of the area corresponding to the predetermined area from the second fundus image;

a third extracting unit configured to extract the area other than the area corresponding to the predetermined area from the third fundus image; and an image combining unit configured to combine the images extracted by the second and the third extracting units.

13. An ophthalmologic apparatus comprising:

a focus index projection system configured to project a focus index on a fundus of the subject's eye;

a moving unit configured to move the focus index projection system outside an optical path; and a changing unit configured to change a light quantity of observation light based on a predetermined area of a fundus image of the subject's eye illuminated by the observation light after the focus index projection system is moved outside the optical path.

14. The ophthalmologic apparatus according to claim 13, further comprising an acquiring unit configured to acquire the fundus image of the subject's eye illuminated by the observation light with the changed light quantity, wherein the predetermined area is an area corresponding to an optic papilla of the fundus of the subject's eye.

15. An ophthalmologic apparatus comprising:

a changing unit configured to change a light quantity of an photographing light based on a predetermined area of a first fundus image of a subject's eye illuminated by an observation light; and an acquiring unit configured to acquire a second fundus image of the subject's eye illuminated by the photographing light with the changed light quantity.

16. The ophthalmologic apparatus according to claim 15, wherein the predetermined area is an area corresponding to a macula of the fundus of the subject's eye.

17. The ophthalmologic apparatus according to claim 16, further comprising: an extraction unit configured to extract the area corresponding to the macula from the first fundus image, wherein the changing unit changes the light quantity of the photographing light based on the area corresponding to the macula.

18. The ophthalmologic apparatus according to claim 16, further comprising a calculating unit configured to calculate the light quantity of the photographing light based on the area corresponding to the macula, wherein the changing unit changes the light quantity of the photographing light based on a calculated result of the calculating unit.

19. An ophthalmologic apparatus comprising:

an observation light source configured to generate observation light;

an photographing light source configured to generate photographing light; and an image combining unit configured configure to combine a part of a first fundus image of a subject's eye illuminated by the observation light and a part of a second fundus image of the subject's image illuminated by the photographing light based on a difference between color temperature of the photographing light and a color temperature of the observation light.

* * * * *